United States Patent
Choi

(10) Patent No.: US 9,314,202 B2
(45) Date of Patent: Apr. 19, 2016

(54) METHOD FOR ANALYZING NERVE FIBER DISTRIBUTION AND MEASURING NORMALIZED EVOKED COMPOUND ACTION ELECTRIC POTENTIAL

(71) Applicant: National Chiao Tung University, Hsinchu (TW)

(72) Inventor: Charles Tak Ming Choi, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 169 days.

(21) Appl. No.: 14/014,788

(22) Filed: Aug. 30, 2013

(65) Prior Publication Data

US 2014/0066803 A1 Mar. 6, 2014

(30) Foreign Application Priority Data

Aug. 30, 2012 (TW) .............................. 101131509 A

(51) Int. Cl.
*A61B 5/00* (2006.01)
*A61B 5/04* (2006.01)
*A61N 1/05* (2006.01)
*A61N 1/36* (2006.01)

(52) U.S. Cl.
CPC ........... *A61B 5/4005* (2013.01); *A61B 5/04001* (2013.01); *A61N 1/0541* (2013.01); *A61N 1/36032* (2013.01)

(58) Field of Classification Search
CPC ............. A61B 5/4005; A61B 5/04001; A61B 5/0484; A61B 5/04845; A61B 5/04842; A61B 5/04847; A61N 1/0541; A61N 1/36032; A61N 1/3605; A61N 1/36185

USPC ......... 600/544, 545, 554; 607/48, 56, 57, 137
See application file for complete search history.

(56) References Cited

U.S. PATENT DOCUMENTS

2008/0221640 A1 9/2008 Overstreet et al.
2008/0300655 A1* 12/2008 Cholette ......................... 607/60
2015/0018699 A1* 1/2015 Zeng et al. .................... 600/509

OTHER PUBLICATIONS

Clay, et al. "Adaptation of the electrically evoked compound action potential (ECAP) recorded from nucleus Cl24 cochlear implant users." Ear and hearing 28.6 (2007): 850-861.*

(Continued)

*Primary Examiner* — Devin Henson
*Assistant Examiner* — David J McCrosky
(74) *Attorney, Agent, or Firm* — Mintz Levin Cohn Ferris Glovsky and Popeo, P.C.; Peter F. Corless; Steven M. Jensen

(57) ABSTRACT

A method for analyzing nerve fibers distribution is provided, including inputting a stimulation signal into a nerve tissue through at least two sensing and conducting electrodes, applying a stimulation signal ratio to control the stimulation signal using an electric current steering technique to electrically stimulate a plurality of nerve fibers within a plurality of stimulations areas of the nerve tissue; receiving a plurality of evoked compound action potentials (ECAP) using at least two sensing and conducting electrodes due to the nerve fibers electrically stimulated and computing a distance between the nerve fiber and the conducting electrodes including eliminating non-ideal effect caused by an electric potential attenuation factor, wherein the electric potential attenuation factor is a function of the distance between each of the conducting electrodes and the nerve tissue; and integrating and comparing the received ECAPs and analyzing the nerve fibers distribution of the nerve tissue.

19 Claims, 20 Drawing Sheets

(56) References Cited

OTHER PUBLICATIONS

Choi, et al. "Conditions for generating virtual channels in cochlear prosthesis systems." Annals of biomedical engineering 37.3 (2009): 614-624.*

Wilson, et al. "Cochlear implants: current designs and future possibilities." J Rehabil Res Dev 45.5 (2008): 695-730.*

Hughes et al., "Electrically Evoked Compound Action Potential Measures for Virtual Channels Versus Physical Electrodes", Ear & Hearing, vol. 32, No. 3, pp. 323-330 (2011).

* cited by examiner

METHOD FOR ANALYZING NERVE FIBER DISTRIBUTION AND MEASURING NORMALIZED EVOKED COMPOUND ACTION ELECTRIC POTENTIAL

CROSS-REFERENCES TO RELATED APPLICATIONS

This application claims under 35 U.S.C. §119(a) the benefit of Taiwanese Application No. 101131509, filed Aug. 30, 2012, the entire contents of which is incorporated herein by reference.

BACKGROUND OF THE INVENTION

1. Field of the Invention

The present invention relates to methods for analyzing nerve fibers distribution, and, more specifically, to a method for analyzing nerve fibers distribution using both the electric current steering technique and the normalized evoked compound action potential (ECAP) technique.

2. Description of Related Art

The electric current steering technique has been applied to cochlear implant (CI) stimulating strategies. In addition, the normalized evoked compound action potential (ECAP) technique has also been used to measure for the neural response in cochlear implant patients.

Referring now to FIG. 1, FIG. 1 shows a schematic diagram depicting the existing ECAP technique. As shown in FIG. 1, an electric current is injected into the group of nerve fibers Nf through the conducting electrode n (El.n). The conducting electrode n+1 (El.n+1) is used to measure and record action potentials Vs of the group of nerve fibers within the stimulation area.

U.S. Patent Application Publication No. 2008/0221640A1 discloses a multi-channel method to elicit electrically-evoked compound action potential (ECAP).

However, it is not possible to use the ECAP technique alone to estimate neural survival based on FIG. 1 or the U.S. Patent Application Publication No. 2008/0221640A1. In other words, even if the stimulation area of FIG. 1 or the U.S. Patent Application Publication No. 2008/0221640A1 covers various nerve fibers, it cannot be rapidly and precisely determined which group of nerve fibers is being activated.

That is to say, the plurality of conducting electrodes are used as the output conducting electrodes (such as El.n+1, El.n+2 and so on). The distance between the group of nerve fibers Nf and each of the plurality of sensing and conducting electrodes may not be the same. Accordingly, the distance between the group of nerve fibers Nf and each of the plurality of sensing and conducting electrodes cannot be precisely computed by the existing techniques.

It can be seen that the existing ECAP technique alone cannot be applied to directly computing a neural distribution. Accordingly, solutions to the problems described above have been long sought, but prior developments have not taught or suggested any solutions and, thus, solutions to the problems have long eluded those skilled in the art. Therefore, there is a heretofore-unaddressed need to overcome defects and shortcomings described above.

SUMMARY OF THE INVENTION

In light of the foregoing drawbacks, an objective of the present invention is to provide a method for rapidly and precisely measuring and analyzing nerve fibers distribution within a nerve tissue. In addition, another objective of the present invention is to provide a method for measuring a normalized evoked compound action potential (ECAP) and estimating a threshold potential level, a comfort potential level and a most comfort potential level of an electrical stimulation signal for each electrode for a patient.

In accordance with the above objectives and other objectives, the present invention provides a method for analyzing nerve fibers distribution using a plurality of sensing and conducting electrodes on the surrounding of or inside a nerve tissue, comprising the steps of (1) inputting a stimulation signal into the nerve tissue through at least two of the plurality of sensing and conducting electrodes, applying a stimulation signal ratio to control the stimulation signal using an electric current steering technique to form at least one of a plurality of stimulation areas in the nerve tissue based on the stimulation signal ratio and forming each of a plurality of evoked compound action electric potentials (ECAP) corresponding to each of the plurality of stimulation areas based on the stimulation signal; (2) receiving the plurality of ECAPs using at least two the plurality of sensing and conducting electrodes; and (3) integrating and comparing the received plurality of ECAPs and analyzing the nerve fibers distribution of the nerve tissue based on an electric potential attenuation factor, a relative distribution of each of the plurality of sensing and conducting electrodes and a distance between the nerve fibers and each of the plurality of sensing and conducting electrodes within each of the plurality of stimulation areas.

Moreover, the present invention also provides a method for analyzing nerve fibers distribution, comprising the steps of: (1) inputting a stimulation signal into a nerve tissue through at least two of a plurality of sensing and conducting electrodes, applying a stimulation signal ratio to control the stimulation signal using an electric current steering technique to electrically stimulate a plurality of nerve fibers within a plurality of stimulation areas of the nerve tissue; (2) receiving a plurality of ECAPs using at least two of the plurality of sensing and conducting electrodes due to the plurality of nerve fibers electrically stimulated and computing a distance between the nerve fibers and at least two of the plurality of sensing and conducting electrodes including eliminating non-ideal effect caused by an electric potential attenuation factor, wherein the electric potential attenuation factor is a function of the distance between the nerve tissue and at least two of the plurality of sensing and conducting electrodes; and (3) integrating and comparing the received plurality of ECAPs and analyzing the nerve fibers distribution in the nerve tissue.

The present invention further provides a method for measuring a normalized ECAP, comprising the steps of (1) inputting a voltage signal into the nerve tissue through at least one of a plurality of sensing and conducting electrodes, and computing a distribution angle corresponding to each of the plurality of sensing and conducting electrodes that are not used for inputting the voltage signal into the nerve tissue; (2) computing a distance between the nerve fibers and each of the plurality of sensing and conducting electrodes based on the distribution angle corresponding to each of the plurality of sensing and conducting electrodes; (3) inputting a stimulation signal into the nerve tissue through at least one of the plurality of sensing and conducting electrodes to generate the plurality of ECAPs, receiving the plurality of ECAPs using the other one of the plurality of sensing and conducting electrodes that are not used for inputting the stimulation signal into the nerve tissue, and receiving the plurality of ECAPs corresponding to the other one of the plurality of sensing and conducting electrodes, based on the plurality of ECAPs, the distance between the nerve fibers and each of the plurality of sensing and conducting electrodes and an electric potential attenuation factor; and (4) computing the received plurality of ECAPs to obtain an average ECAP of the nerve fibers.

In addition, the present invention also provides a method for using a normalized ECAP, comprising the steps of (1) inputting a voltage signal into the nerve tissue through a plurality of sensing and conducting electrodes, and computing an average ECAP corresponding to a distance between the plurality of sensing and conducting electrodes and the nerve tissue based on the method for measuring a normalized ECAP; (2) generating a curve of each of the plurality of sensing and conducting electrodes corresponding to the average ECAP; (3) obtaining a threshold potential and a comfort potential of the potential signal inputted into the nerve tissue, and obtaining a first correlation between the average ECAP and the threshold potential and a second correlation between the average ECAP and the comfort potential; (4) generating the threshold potential level and the comfort potential level of each of the plurality of sensing and conducting electrodes based on the first correlation, the second correlation and the threshold potential and the comfort potential of the potential signal.

Accordingly, the plurality of sensing and conducting electrodes of the present invention is used for inputting a stimulation signal into a nerve tissue by combining the normalized ECAP technique and the electric current steering technique. A plurality of stimulation areas in the nerve tissue is dynamically generated. Each of a plurality of ECAPs corresponding to each of the plurality of stimulation areas is formed based on the stimulation signal. The received plurality of ECAPs is integrated and compared in order to rapidly and precisely analyze a nerve fibers distribution of the nerve tissue.

Besides, the normalized ECAP is used in the objective measurement method. A threshold potential level and a most comfort potential level of an electrical stimulation signal for a patient may be estimated without requiring the patient to respond. It would be very useful that the electric current stimulation factor may be rapidly and precisely determined accordingly to the present invention.

Certain embodiments of the present invention have other methods or components in addition to or in place of those mentioned above. The methods or components will become apparent to those skilled in the art from a reading of the following detailed description when taken with reference to the accompanying drawings.

BRIEF DESCRIPTION OF THE DRAWINGS

The present invention can be more fully understood by reading the following detailed descriptions of the preferred embodiments, with reference made to the accompanying drawings, wherein.

DETAILED DESCRIPTION

The present invention is described by the following specific embodiments. Those with ordinary skills in the arts can readily understand the other advantages and functions of the present invention after reading the disclosure of this specification. The present invention can also be implemented with different embodiments. Various details described in this specification can be modified based on different viewpoints and applications without departing from the scope of the present invention.

Figure 8A:
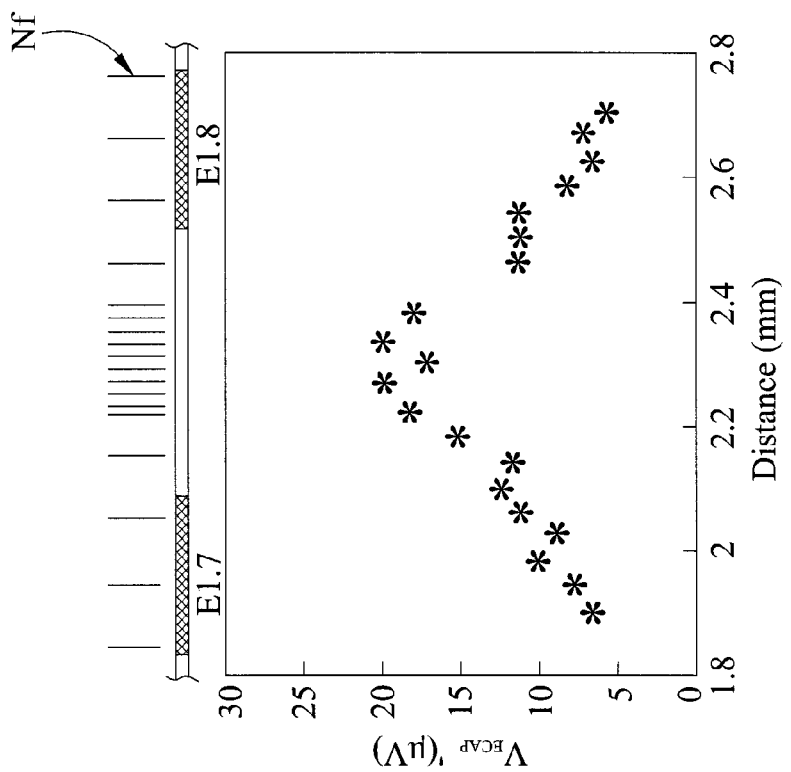
FIGS. 8A-8C show line graphs of normalized ECAP amplitudes vs. centroids of stimulation areas according to three examples of the present invention.
Figure 8B:
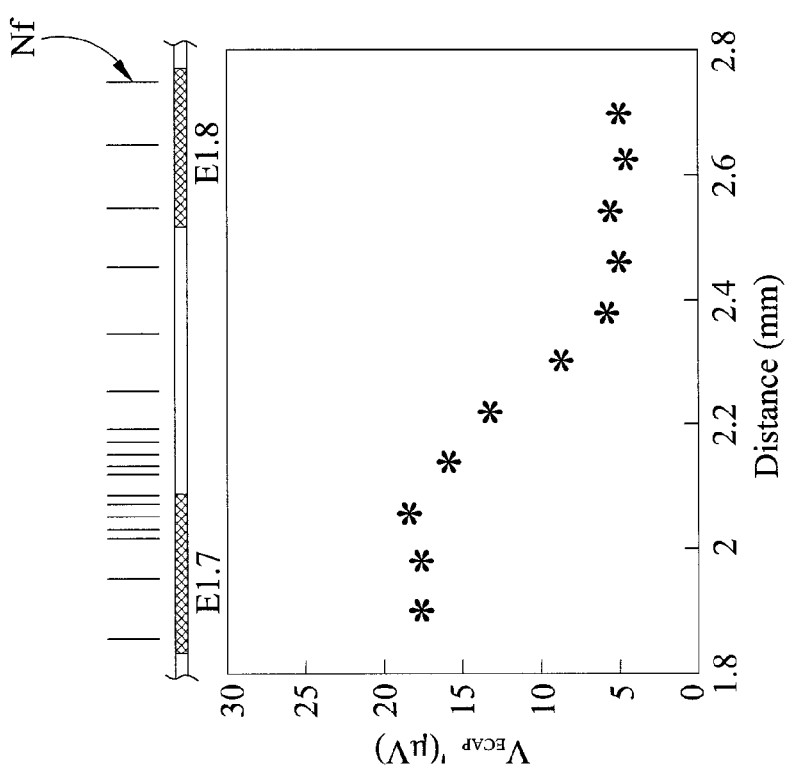
Figure 8C:
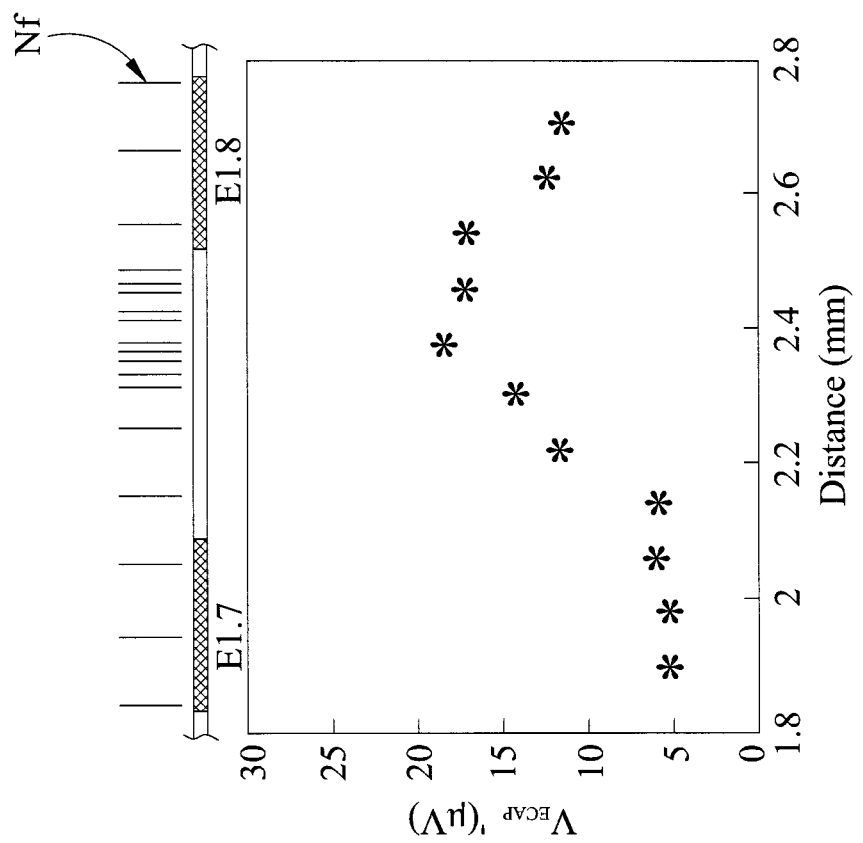
Figure 9:
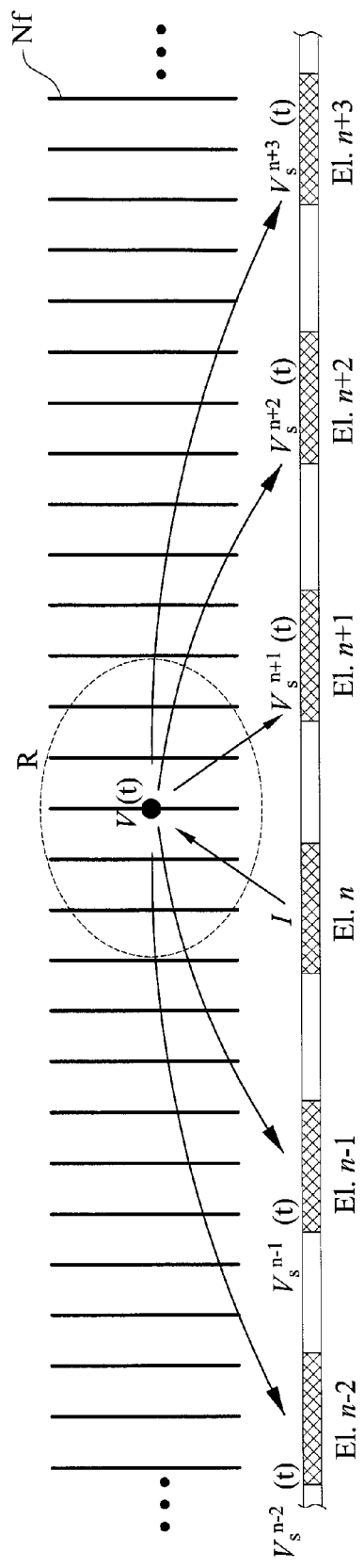
FIG. 9 is a schematic diagram illustrating the ECAP technique according to the present invention.
Figure 10A:
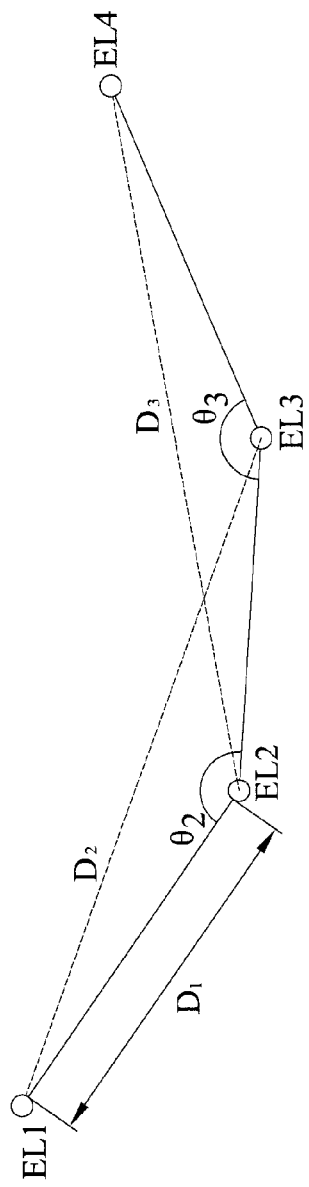
FIGS. 10A and 10B are schematic diagrams illustrating the triangulation technique according to the present invention.

The present invention provides a method for analyzing nerve fibers distribution and a method for measuring a normalized evoked compound action electric potential (ECAP). The method of analyzing nerve fibers distribution is shown in FIGS. 2-8. Moreover, the method for measuring a normalized ECAP is shown in FIGS. 9-11.

Figure 1:
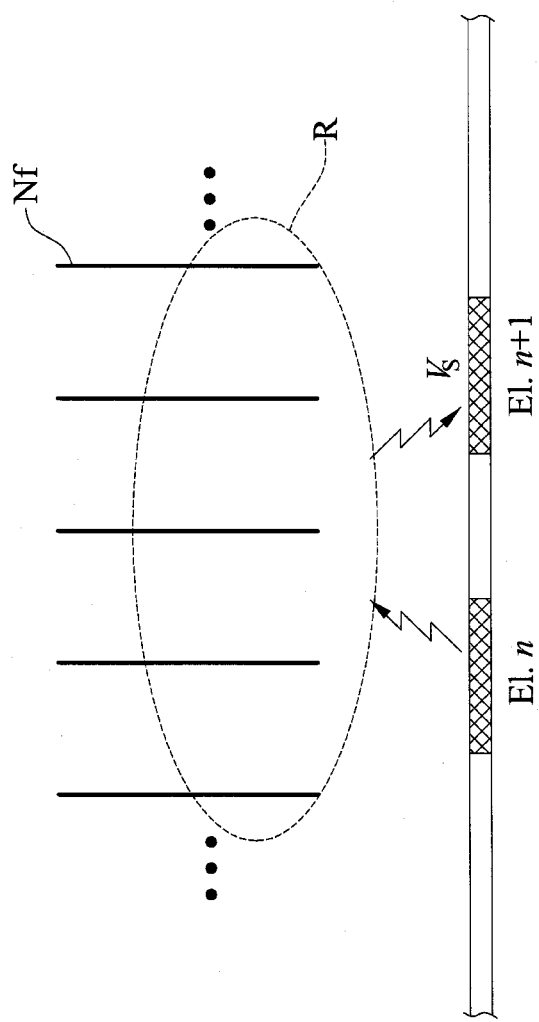
FIG. 1 is a schematic diagram depicting the existing evoked compound action potential (ECAP) technique.
Figure 2:
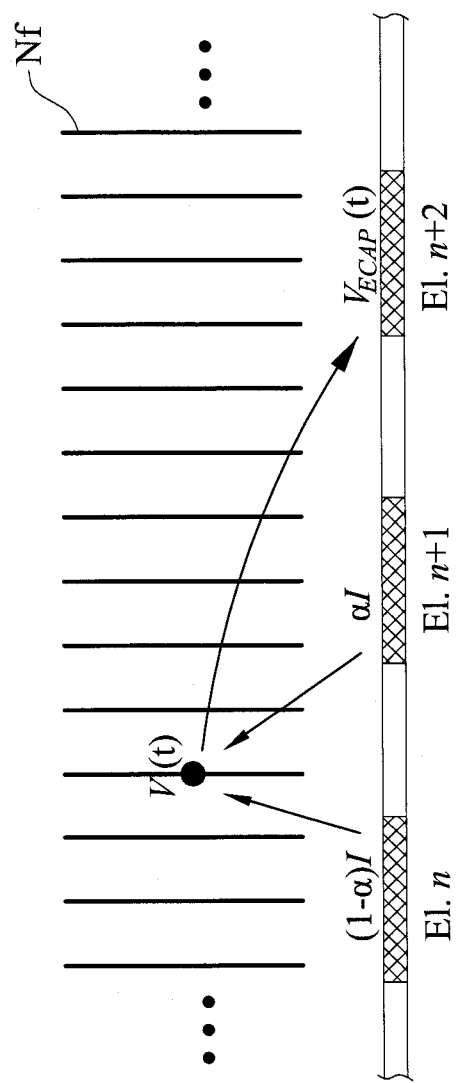
FIGS. 2 and 3 are schematic diagrams illustrating a method for analyzing nerve fibers distribution using an electric current steering technique according to the present invention.
Figure 3:
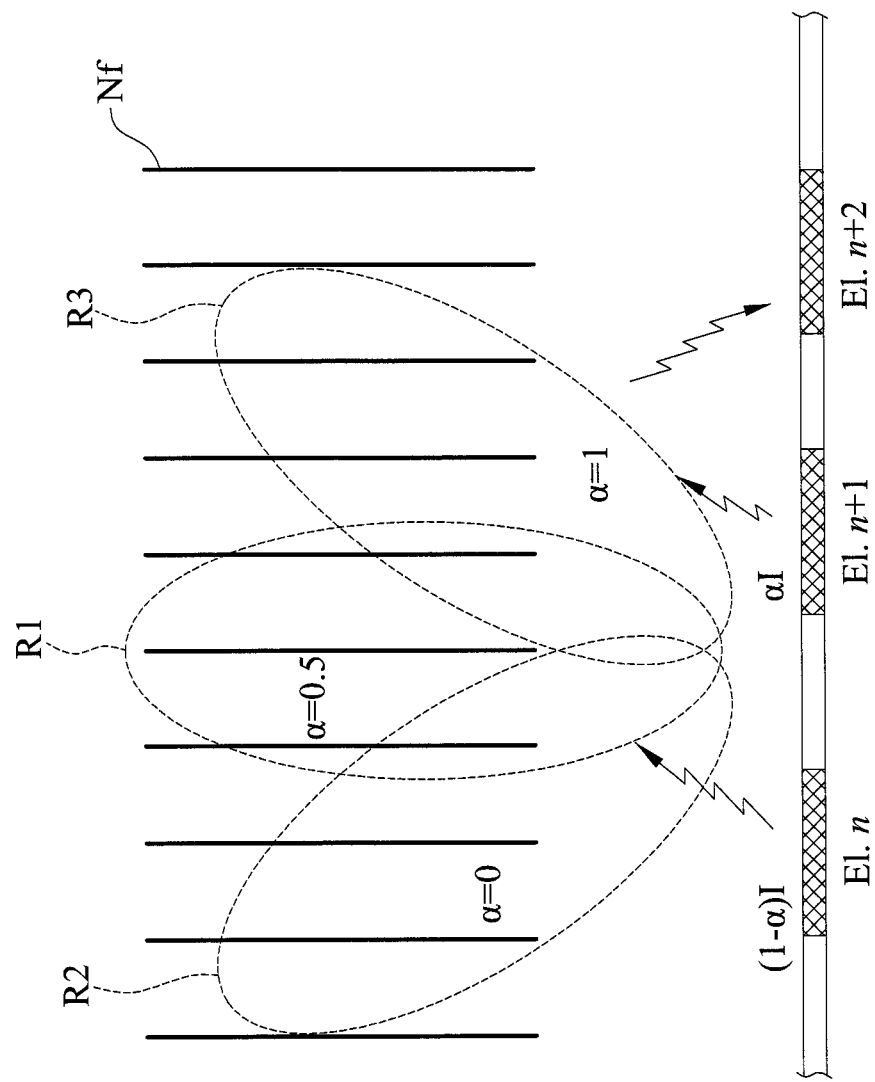

According to the present invention, referring to FIGS. 2 and 3, the electric current steering technique is used in the method for analyzing nerve fibers distribution. Multiple straight lines illustrated in FIGS. 2 and 3 may represent a group of nerve fibers Nf, such as auditory nerve fibers, vagus nerve fibers, retinal nerve fibers and spinal cord nerve fibers. Multiple sensing and conducting electrodes El.n, El.n+1, El.n+2 may represent a plurality of sensing and conducting electrodes which is formed into an electrode array.

In practice, a stimulation signal is inputted into a nerve tissue through at least two of the plurality of conducting electrodes. A stimulation signal ratio is applied to control the stimulation signal using an electric current steering technique in order to form at least one of a plurality of stimulation areas in the nerve tissue and to form at least one of a plurality of ECAPs corresponding to at least one of the plurality of stimulation areas based on the stimulation signal ratio.

According to one embodiment of the present invention, as shown in FIG. 3, the conducting electrodes El.n, El.n+1 may be used as the input conducting electrodes. An action potential/voltage is created by the conducting electrodes El.n, El.n+1 within the plurality of nerve fibers Nf within a stimulation area R1. The stimulation signal ratio $\alpha=0.5$ is applied to control the stimulation signal using an electric current steering technique through the conducting electrodes El.n, El.n+1.

In other words, the input electric currents of the conducting electrodes El.n, El.n+1 are 0.5I, where I represents the biphasic current pulse. Additionally, a virtual electrode (not shown) is formed between the conducting electrodes El.n, El.n+1. If the plurality of nerve fibers Nf within the first stimulation area R1 is survived and works properly, the action potential/voltage V(t) generated in the nerve fibers is then coupled to the conducting electrode El.n+2. $V_{ECAP}(t)$ represents the coupling of the action potential V(t) of all the excited nerve fibers to the conducting electrode El.n+2. Additionally, $V_{ECAP}(t)$ is directly proportional to the number of nerve fibers being excited by the stimulation signal through the conducting electrodes El.n, El.n+1. Accordingly, the neural survival in the cochlea can be measured based on $V_{ECAP}(t)$.

Subsequently, according to another embodiment of the present invention, as shown in FIG. 3, the stimulation signal ratio α=0 is applied to control the stimulation signal using an electric current steering technique through the conducting electrodes El.n, El.n+1. An action potential/voltage is created by the conducting electrodes El.n, El.n+1 within the plurality of nerve fibers Nf of a second stimulation area R2. Moreover, a virtual electrode (not shown) is formed between the conducting electrodes El.n, El.n+1. If the plurality of nerve fibers Nf within the second stimulation area R2 is survived and works properly, the action potential V(t) generated in the nerve fibers is then coupled to the conducting electrode El.n+2. $V_{ECAP}(t)$ is directly proportional to the number of nerve fibers being excited by the stimulation signal through the conducting electrodes El.n, El.n+1.

Further, according to an alternative embodiment of the present invention, as shown in FIG. 3, the stimulation signal ratio α=1 is applied to control the stimulation signal using an electric current steering technique through the conducting electrodes El.n, El.n+1. An action potential/voltage is created by the conducting electrodes El.n, El.n+1 within the plurality of nerve fibers Nf of a third stimulation area R3. Moreover, a virtual electrode (not shown) is formed between the conducting electrodes El.n, El.n+1. If the plurality of nerve fibers Nf within the third stimulation area R3 is survived and works properly, the action potential V(t) generated in the nerve fibers is then coupled to the conducting electrode El.n+2. $V_{ECAP}(t)$ is proportional to the number of nerve fibers being excited by the stimulation signal through the conducting electrodes El.n, El.n+1. Therefore, it can be seen from FIG. 3 that the first stimulation area R1, the second stimulation area R2 and the third stimulation area R3 within the nerve tissue may be overlapped or may not be overlapped.

Specifically, the group of nerve fibers are electrically stimulated within a plurality of stimulation areas of the nerve tissue in order to receive a plurality of ECAPs. Electrical stimulation may be performed by probe only stimulation, masker only stimulation, masker and probe stimulation or no masker and probe stimulation in order to remove switch on artifact.

Figure 4A:
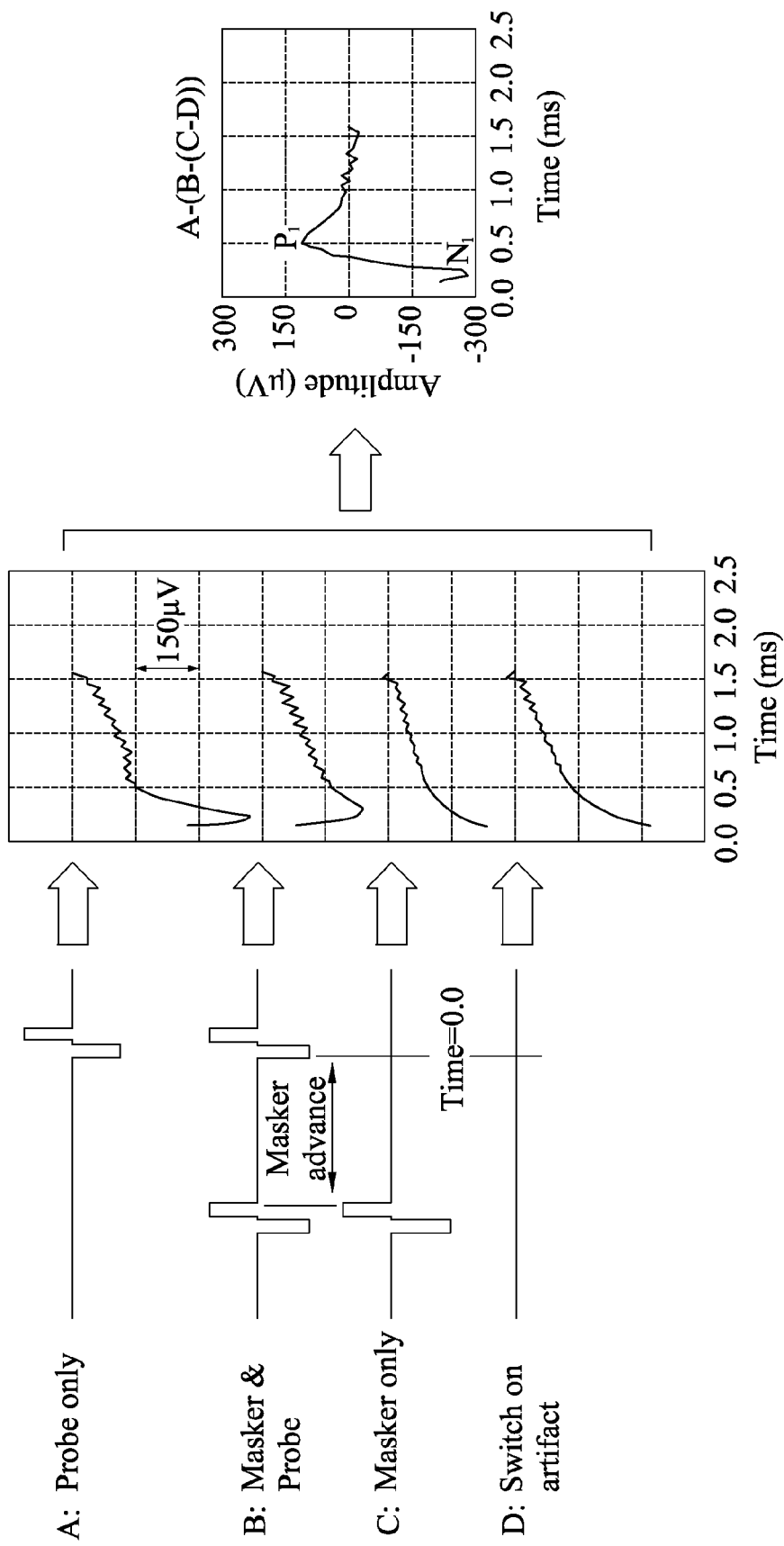
FIGS. 4A and 4B are schematic diagrams illustrating two procedures for removing artifacts during ECAP measurements based on prior art.

Accordingly, the received plurality of ECAPs is optimized. As shown in FIG. 4A, probe only stimulation is labeled as A, Masker and probe stimulation is labeled as B, Masker only stimulation is labeled as C, and No masker and probe stimulation is labeled as D. Once A−(B−(C−D)) is computed, noise and switch on artifact can be removed. Consequently, an optimized result is obtained.

Figure 4B:
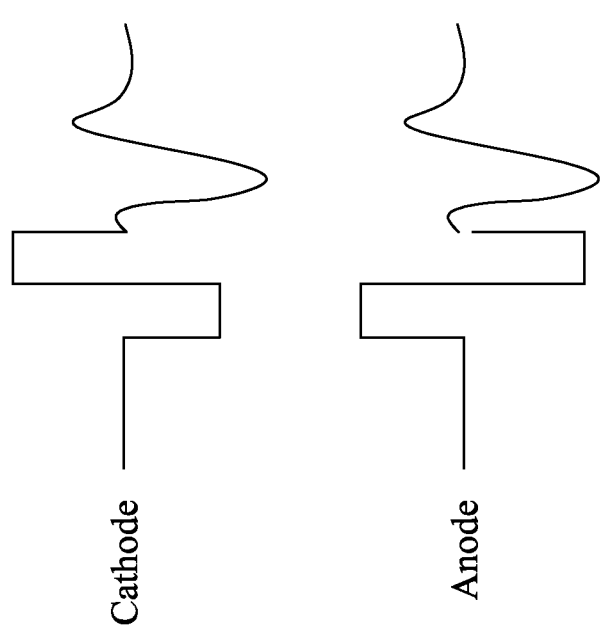

As shown in FIG. 4B, according to one embodiment of the present invention, the alternating polarity method may be used to remove noise and switch on artifact. With this method, noise can be removed by the average of the plurality of ECAPs generated based on anodic and catholic stimulation.

According to the present invention, referring to FIGS. 2 and 3, the first stimulation area R1, the second stimulation area R2 and the third stimulation area R3 are formed by using the electric current steering technique by controlling the α to 0.5, 0 and 1, respectively. More stimulation areas can be formed by using the electric current steering technique and changing the α repeatedly. The group of nerve fibers within the specific areas of the nerve tissue may be covered by at least one stimulation area in order to further determine whether the group of nerve fibers within the specific areas of the nerve tissue is being activated.

Figure 5:
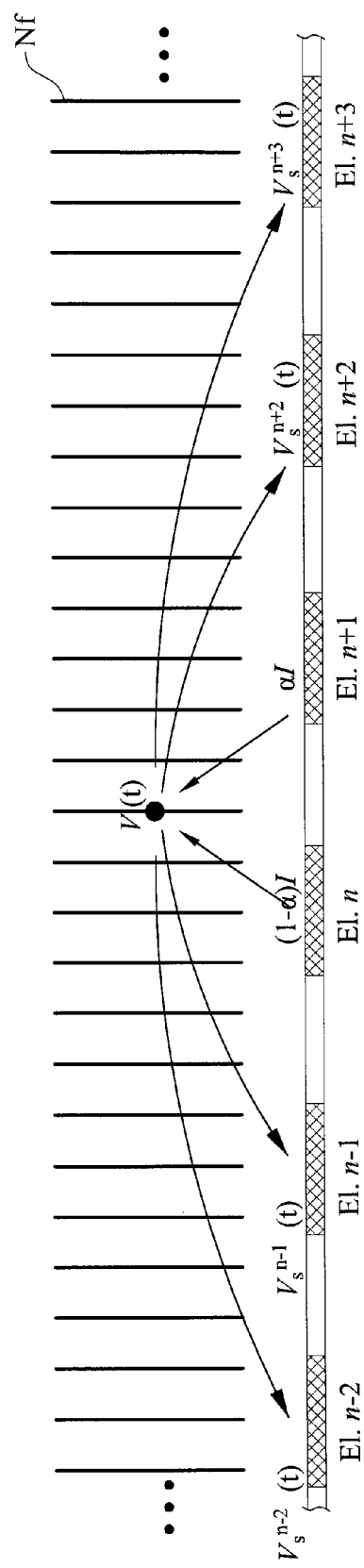
FIG. 5 is a schematic diagram illustrating a method for analyzing nerve fibers distribution according to the present invention.

Subsequently, referring to FIG. 5, FIG. 5 shows a schematic diagram illustrating a method for analyzing nerve fibers distribution according to the present invention. The conducting electrodes El.n, El.n+1 are used as the input conducting electrodes. An electric current divided in the electric current ratio αI:(1−α)I is inputted into the nerve tissue through the conducting electrodes El.n, El.n+1. In addition, the conducting electrodes El.n−2, El.n−1, El.n+2, El.n+3 may be used as the sensing (output) conducting electrodes. Electric potentials are received by the conducting electrodes El.n−2, El.n−1, El.n+2, El.n+3, but may be attenuated due to a non-ideal factor. The electric potentials received by the conducting electrodes El.n−2, El.n−1, El.n+2, El.n+3 can be represented as equation (1). $V_{ECAP}(t)$ can be obtained and represented by equation (2), where V(t) represents the source action potential/voltage generated within the stimulation area R and t represents time. The electric potentials $V_s^{n-2}(t)$, $V_s^{n-1}(t)$, $V_s^{n+2}(t)$, $V_s^{n+3}(t)$ are the voltage signal received through the sensing conducting electrodes El.n−2, El.n−1, El.n+2, El.n+3, respectively, where DecayFactor(Dn) represents a non-ideal factor and $D_n$ represent the distance between the nth conducting electrode and the nerve fibers within the stimulation area R. It should be noted that the number of the plurality of output conducting electrodes are not limited to 4. In other words, the number of the plurality of output conducting electrodes may be 2 or more.

Equations (1) and (2) are expressed as follows:

$$V_s^{n-2}(t) = DecayFactor(D_{n-2}) \cdot V(t) \quad (1)$$
$$V_s^{n-1}(t) = DecayFactor(D_{n-1}) \cdot V(t)$$
$$V_s^{n+2}(t) = DecayFactor(D_{n+2}) \cdot V(t)$$
$$V_s^{n+3}(t) = DecayFactor(D_{n+3}) \cdot V(t)$$

$$V'_{ECAP}(t) = \frac{\sum_N V(t)}{N} = \frac{\left(\sum_N \frac{V_s(t)}{DecayFactor(D)}\right)}{N} \quad (2)$$

where $V_{ECAP}(t)$ represents the normalized average of V(t) at the centroid of the stimulation area of the nerve tissue, V(t) represents the source action potential/voltage generated within the stimulation area due to stimulation by El.n and El.n+1, N represents the plurality of output conducting electrodes, and $$DecayFactor(D) = \frac{k1}{D},$$

where k1 represents a constant and DecayFactor(D) is inversely proportional to the distance D between each of the plurality of the output conducting electrodes and each of the nerve fibers Nf within the stimulation area. Since $V_s(t)$ are the only signal we can measure through the sensing electrodes. We use equation (1) to back calculate the source voltage V(t)

in the stimulation area. $V_{ECAP}(t)$ is not ECAP which is typically measured through a sensing electrode, but it represents a normalized ECAP or the average source voltage generated at the stimulation area which does not change with the sensing electrode distance, thus, a normalized ECAP. The normalized ECAP is useful also because if we plot all the normalized ECAP along the nerve fibers, then we have a spatial signal that is proportional to the nerve fibers distribution.

Moreover, if the plurality of conducting electrodes are spherical, the electric potential attenuation factor is directly proportional to the distance between each of the nerve fibers and each of the plurality of conducting electrodes. If the plurality of conducting electrodes are flat-shaped, the electric potential attenuation factor is also proportional to the distance between each of the nerve fibers and each of the plurality of conducting electrodes, but its decay rate is slower than the spherical case.

Figure 6A:
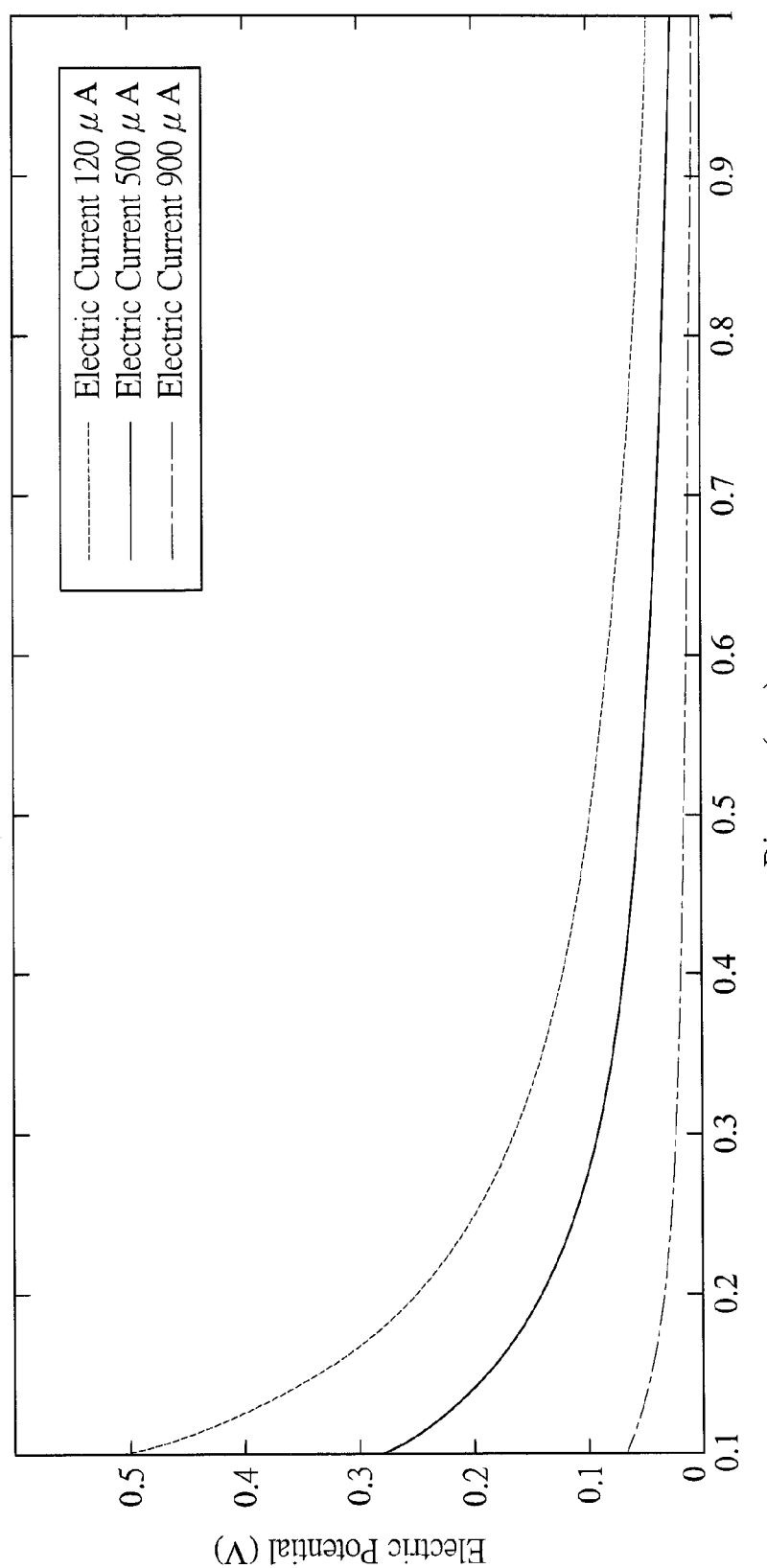
FIG. 6A is a line graph of electric potential vs. distance depicting a plurality of spherical sensing and conducting electrodes which is formed into an electrode array inserted in a nerve tissue according to the present invention.
Figure 6B:
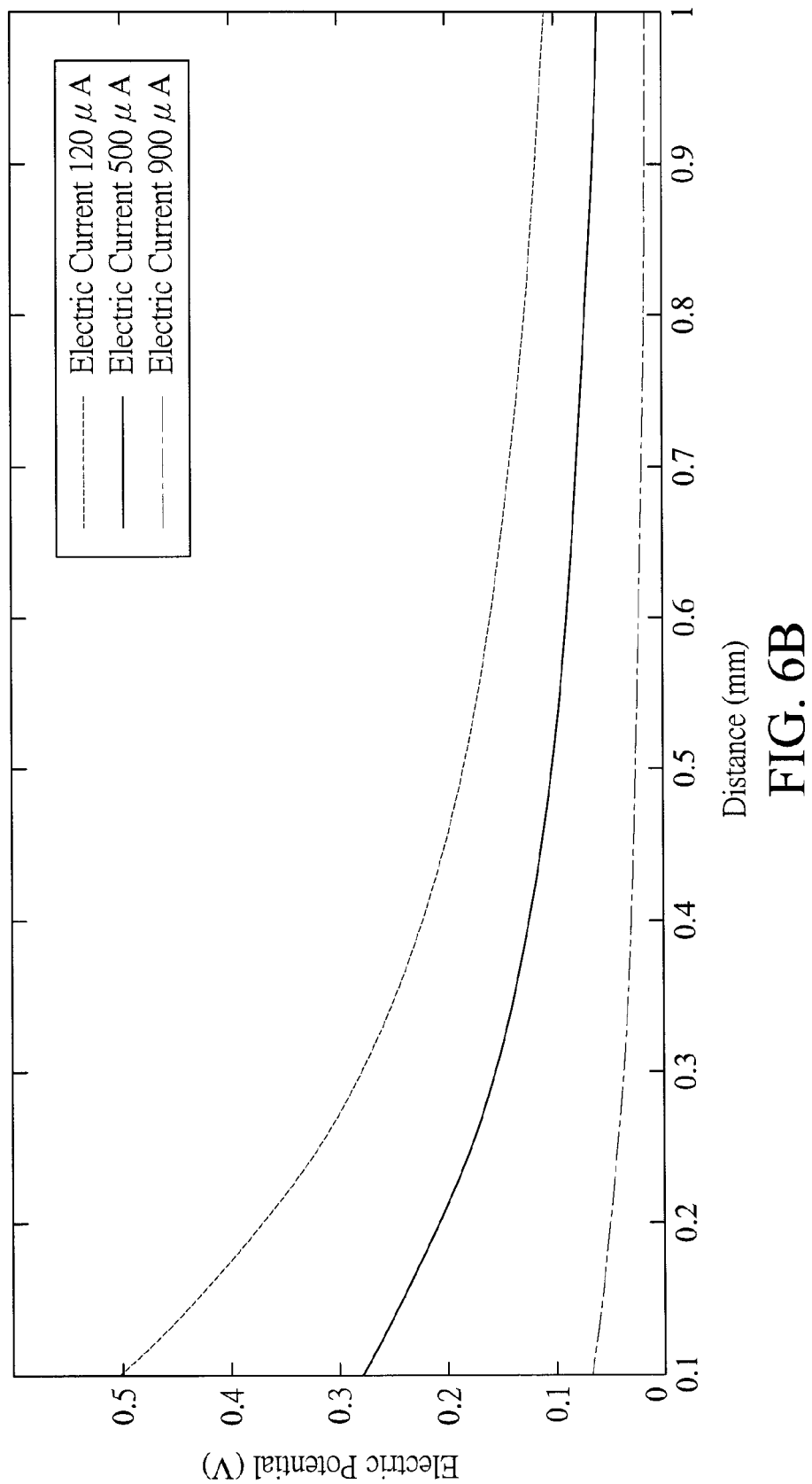
FIGS. 6B-6E are line graphs of electric potential vs. distance depicting a plurality of flat-shaped sensing and conducting electrodes which is formed into an electrode array inserted in a nerve tissue according to the present invention, and also illustrate that an electric current is used as a stimulation signal.
Figure 6C:
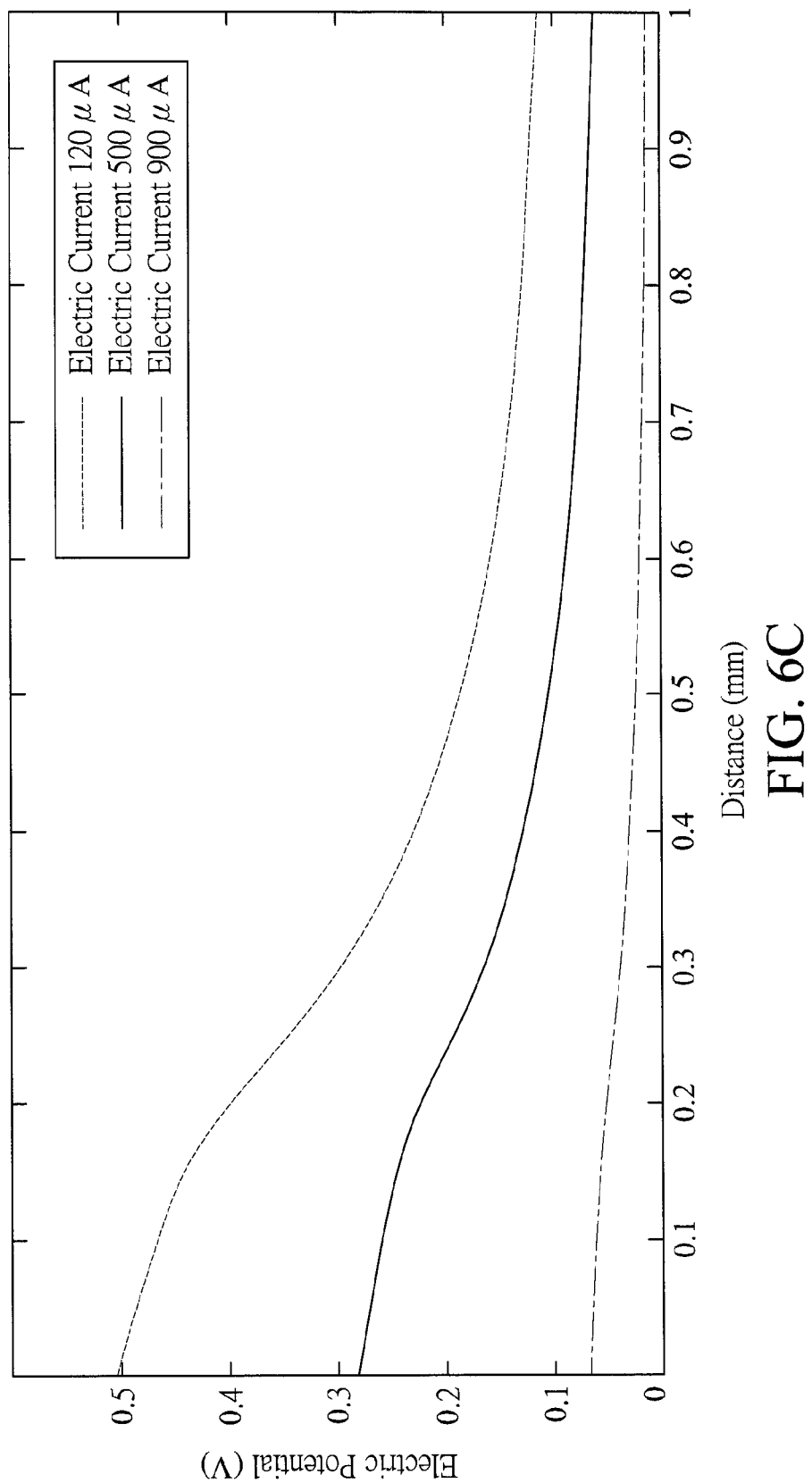
Figure 6D:
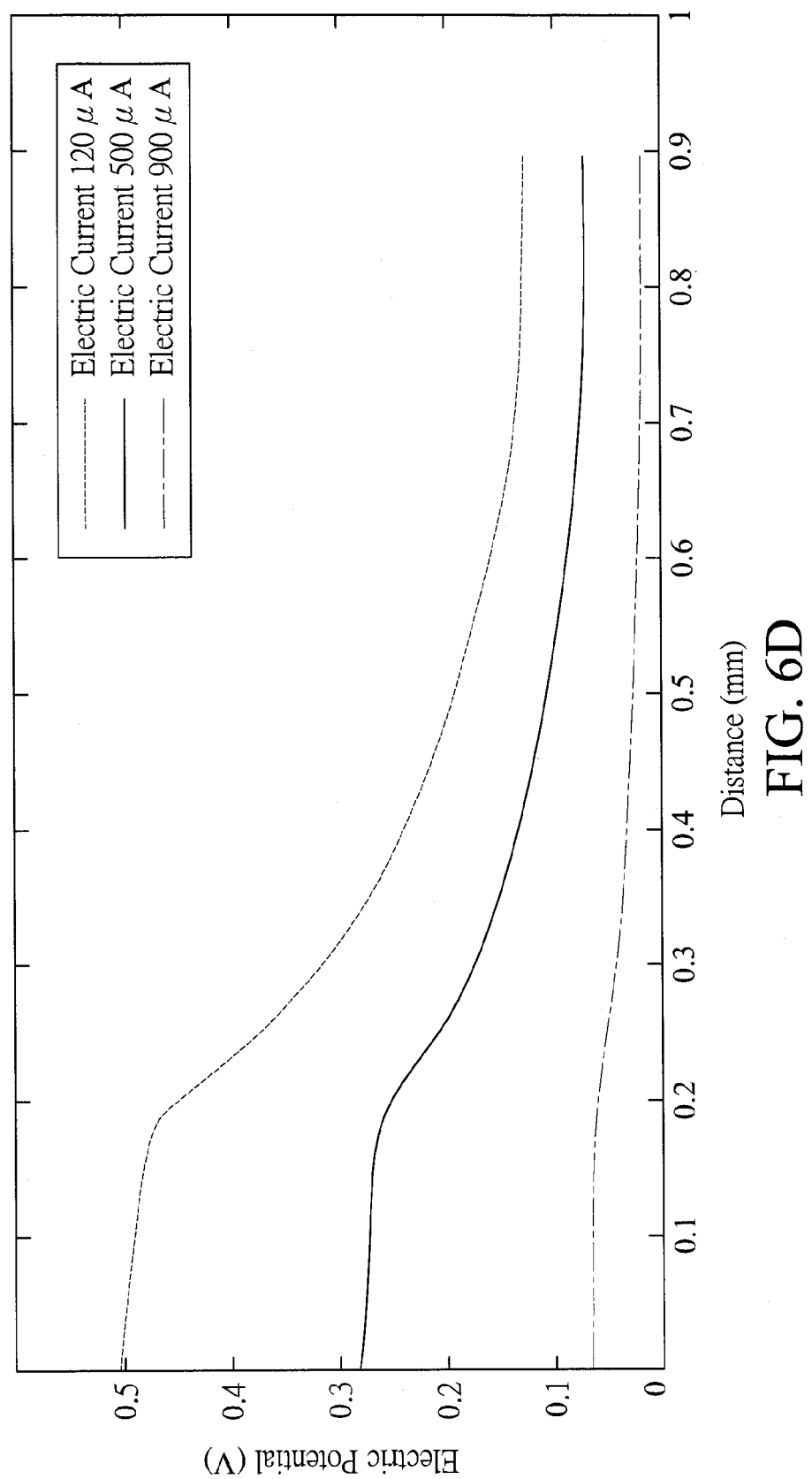
Figure 6E:
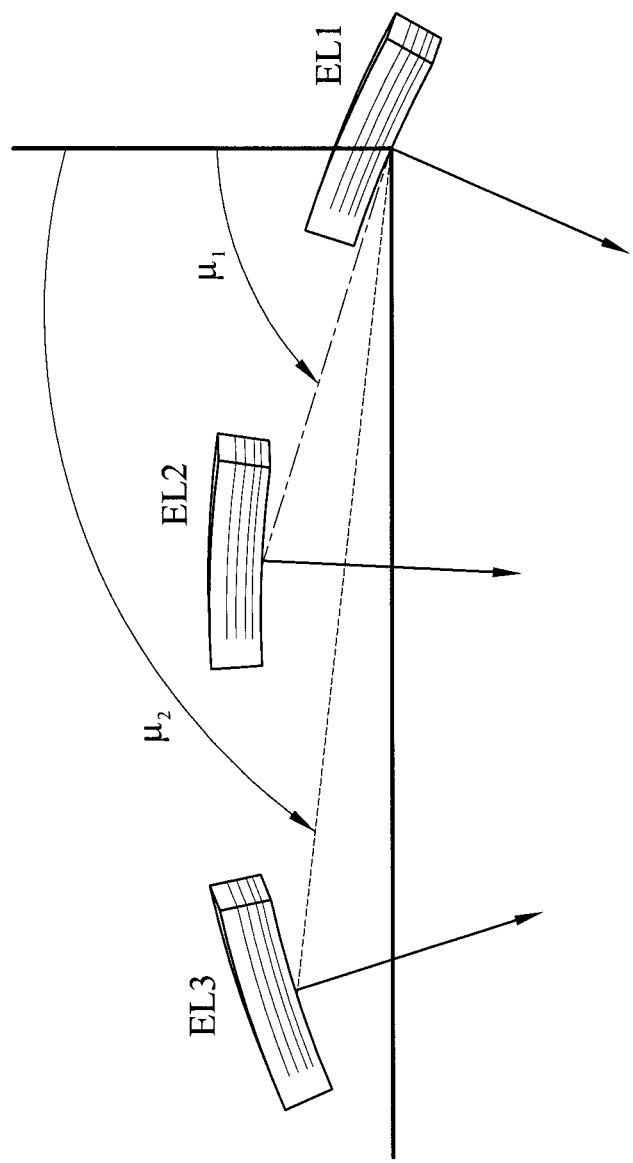

Referring to FIGS. 6A-6E, FIGS. 6A-6E show line graphs of electric potential vs. distance depicting a plurality of flat-shaped/spherical conducting electrodes which is formed into an electrode array inserted in a nerve tissue according to the present invention. As shown in FIG. 6E, the conducting electrode EL1 is used as an input conducting electrode, and the conducting electrodes EL2 and EL3 are used as two output conducting electrodes. The group of nerve fibers is located below the conducting electrodes EL1, EL2 and EL3, as shown in FIG. 6E, where $\mu_1=73.879°$, $\mu_2=83.901°$. Referring to FIGS. 6C and 6D, based on $\mu_1$ and $\mu_2$, a voltage inputted by the conducting electrode EL1 may be attenuated due to the distance between the conducting electrodes EL2 and EL3. Due to the plurality of conducting electrodes being flat-shaped conducting electrodes or spherical conducting electrodes, the voltage may also be attenuated. According to another embodiment of the present invention, an electric current may also be inputted into the nerve tissue through the plurality of conducting electrodes in the application of cochlear prosthesis.

In addition, referring to equations (1) and (2) again, the distances $D_{n-2}$, $D_{n-1}$, $D_{n+2}$ and $D_{n+3}$ between each of the conducting electrodes El.n−2, El.n−1, El.n+2, El.n+3 and the nerve fiber Nf may be respectively obtained prior to receiving $V_{ECAP}(t)$ within the stimulation area of the nerve tissue by equation (2). When the distances $D_{n-2}$, $D_{n-1}$, $D_{n+2}$ and $D_{n+3}$ between each of the conducting electrodes El.n−2, El.n−1, El.n+2, El.n+3 and the nerve fiber Nf are obtained respectively, DecayFactor($D_{n-2}$), DecayFactor($D_{n-1}$), DecayFactor($D_{n+2}$) and DecayFactor($D_{n+3}$) can be obtained by equation (1). Accordingly, V(t) corresponding to each of the voltage measured by sensing conducting electrodes El.n−2, El.n−1, El.n+2 and El.n+3 may be obtained. Therefore, $V_{ECAP}(t)$ can also be obtained by equation (2).

Further, the distances $D_{n-2}$, $D_{n-1}$, $D_{n+2}$ and $D_{n+3}$ between each of the conducting electrodes El.n−2, El.n−1, El.n+2, El.n+3 and the nerve fiber Nf can also be obtained respectively using the triangulation technique.

Figure 7A:
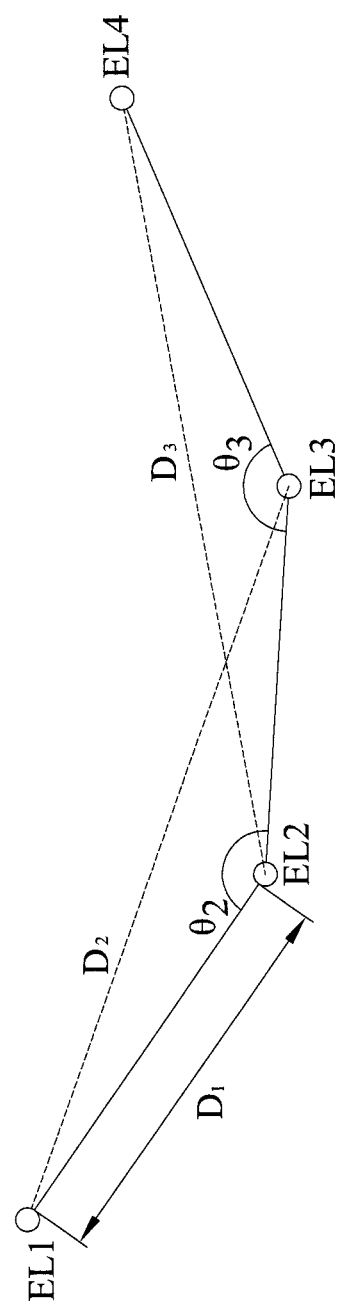
FIGS. 7A and 7D are schematic diagrams illustrating the triangulation technique according to the present invention.
Figure 7B:
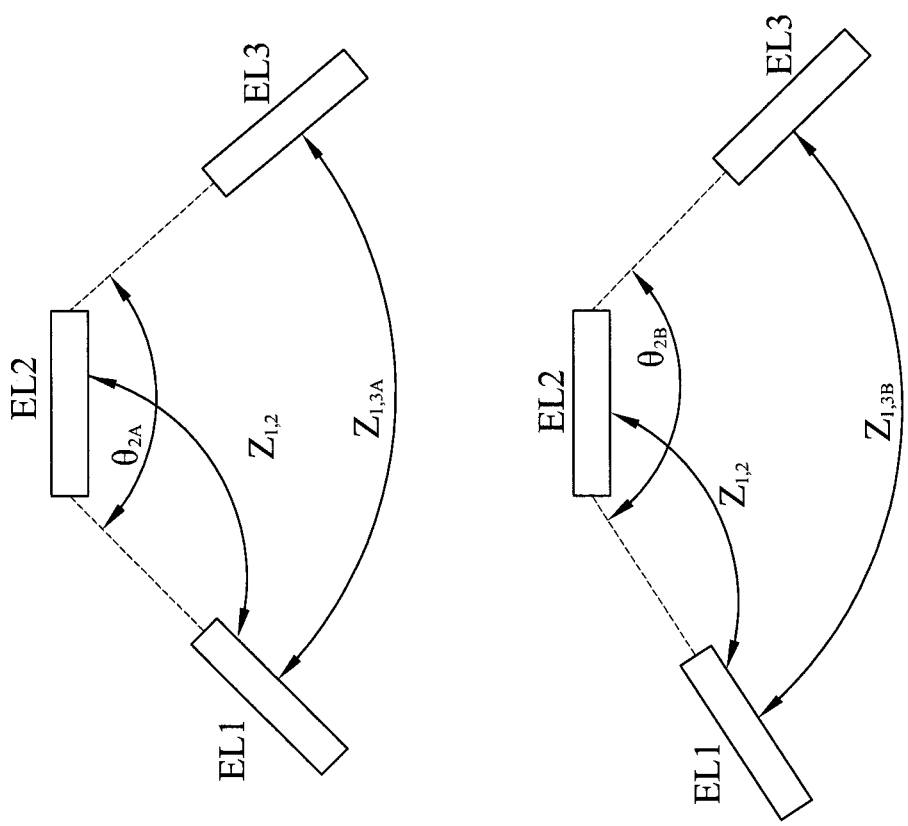
FIGS. 7B and 7C are schematic diagrams illustrating the resistance and angle measurement according to the present invention.
Figure 7C:
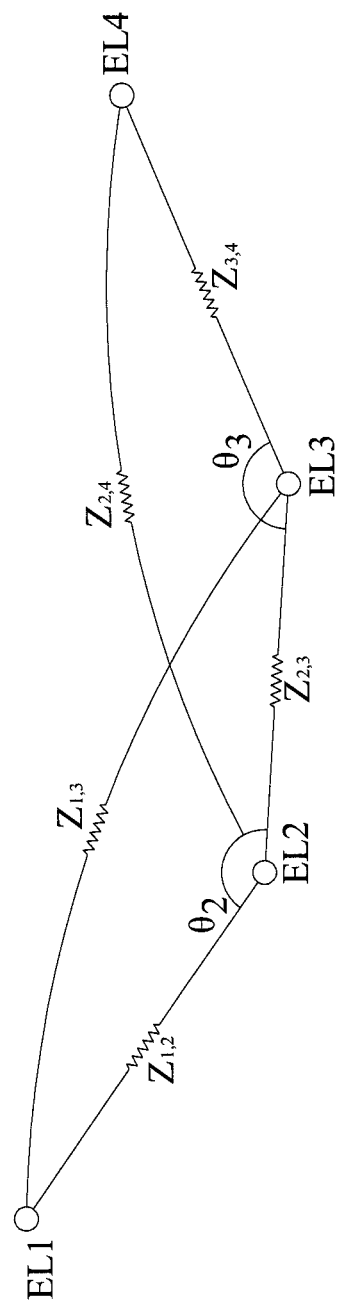

Referring to FIGS. 7A-7D, FIGS. 7A and 7D show schematic diagrams illustrating the triangulation technique according to the present invention. Moreover, FIGS. 7B and 7C show schematic diagrams illustrating the resistance and angle measurement according to the present invention. It should be noted that the plurality of conducting electrodes may not be limited to flat-shaped conducting electrodes or spherical conducting electrodes.

Referring now to FIG. 7A, there are four conducting electrodes. The distance between the adjacent conducting electrodes is given. An electric current I1' is inputted into the nerve tissue through the conducting electrode EL1. The action potential/voltage V1' is not given, or may be generated. Electric potentials V2' and V3' can be received through the conducting electrodes EL2 and EL3. The distance between the conducting electrode EL1 and the conducting electrode EL2 is labeled as D1. The distance between the conducting electrode EL1 and the conducting electrode EL3 is labeled as D2.

According to the electrical impedance equations, $$Z_{1,2} \propto D_1$$

$$Z_{1,3} \propto D_2 \qquad (3)$$

The electrical impedance $Z_{1,2}$, $Z_{1,3}$ is directly proportional to the distances D1, D2, respectively. If a bigger angle is formed by the conducting electrode EL1 and the conducting electrode EL3, the distance between the conducting electrode EL1 and the conducting electrode EL3 will be longer. That is, if $\theta_{2B} > \theta_{2A}$, $Z_{1,3B} > Z_{1,3A}$, as shown in FIG. 7B.

The relationships between the angle and electrical impedance are represented as follows:

$$\theta_2 \propto \frac{Z_{1,3}}{Z_{1,2}} \qquad (4)$$

$$\theta_3 \propto \frac{Z_{2,4}}{Z_{2,3}}$$

Based on the above relationships, the angle $\theta_{2\square}$ can be obtained by the ratio $Z_{1,3}/Z_{1,2}$ and the angle $\theta_{3\square}$ can be obtained by the ratio $Z_{2,4}/Z_{2,3}$ as shown in FIG. 7C. This method is exact if the electrodes are point sources. Since the electrodes are not point sources and have finite dimensions, equation (3) and (4) can be modified based on numerical modeling to improve its accuracy.

Accordingly, the angles $\theta_{D4\square}$ and $\theta_{D5}$ may be computed in order to obtain a distribution angle between the adjacent conducting electrodes. According to another example of the present invention, if the plurality of conducting electrodes EL.1-EL4 are spherical, k2 can be obtain, as shown in FIG. 6A (due to $$V2' = \frac{k2V1'}{D1}, V3' = \frac{k2V1'}{D2},$$

V1', D1, V2', V3' given). Subsequently, D2 and $\theta_{2\square}$ can also be computed. According to alternative example of the present invention, if the conducting electrodes are flat-shaped, the curve fitting method can be used to obtain the attenuation factor and angles of the electric potentials and distance, based on FIGS. 6B-6E. Therefore, D2 and $\theta_{2\square}$ can also be computed.

Figure 7D:
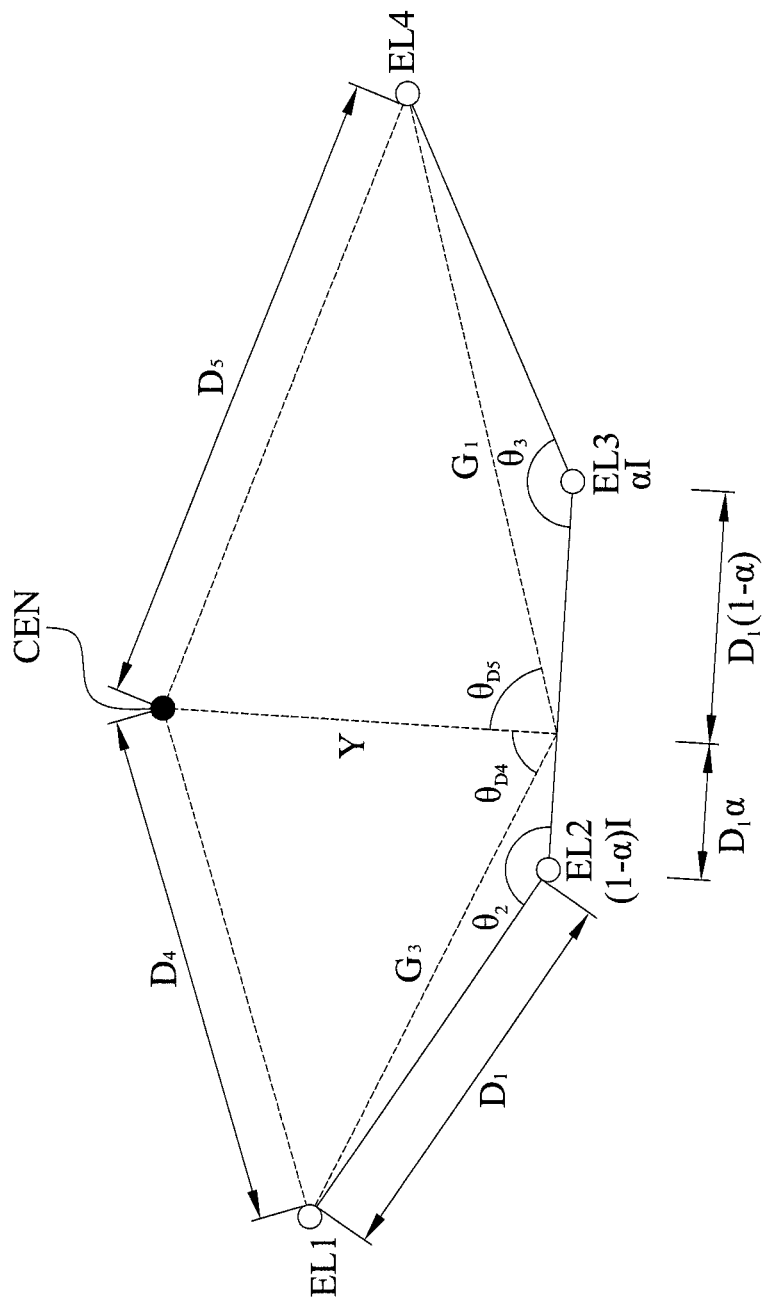

Besides, when the distance between the adjacent conducting electrodes is given, the distance between the centroid of the nerve fiber and each of the plurality of conducting electrodes may also be obtained according to FIG. 7A. Also, as shown in FIG. 7D, the distance between the centroid CEN and the conducting electrode EL1 is labeled as D4. The distance between the centroid CEN and the conducting electrode EL4 is labeled as D5. An electric current ratio $(1-\alpha)I:\alpha I$ is inputted into the nerve tissue through the conducting electrodes EL2, EL3, where I is the electric current source and $\alpha$ is a variable of the electric current ratio. Accordingly, an ECAP Vx is generated in the centroid CEN of the nerve fiber. In addition, electric potentials Vx1 and Vx4 are received through the conducting electrode EL1, EL4, respectively. Consequently, the equation (5) may be obtained as follows:

$$Vx4 \cdot D5 = Vx1 \cdot D4 = k3 \cdot Vx \quad (5)$$

where k3 is a constant, and Vx1 and Vx4 are the electric potentials.

Moreover, the following equation (6) may also be obtained by using the triangulation technique. As shown in FIG. 7D, a particular position is located between the conducting electrode EL2 and the conducting electrode EL3 and therefore the distance Y is between the centroid CEN of the stimulation area and the particular position. Moreover, the distance between the particular position and the conducting electrode EL1 is labeled as G3 and the distance between the particular position and the conducting electrode EL4 is labeled as G1.

$$D5 = \sqrt{Y^2 + G1^2 - 2Y \cdot G1 \cdot \cos\theta_{D5}}$$

$$D4 = \sqrt{Y^2 + G3^2 - 2Y \cdot G3 \cdot \cos\theta_{D4}} \quad (6)$$

In one embodiment of the present invention, the distance Y may be computed by the equation (6) based on G1, G3, $\theta_{D4}$ and $\theta_{D5}$ given. Once the distance Y is obtained, the distances D4 and D5 will also be obtained. Consequently, the ECAP Vx can be obtained by equation (5).

Accordingly, the present invention provides a method for analyzing nerve fibers distribution and a method for measuring a normalized ECAP ($V_{ECAP'}$(t) in equation (2)). In addition, the relationship between the plurality of ECAPs and the plurality of output conducting electrodes may also be analyzed in order to obtain nerve fibers distribution. In other words, the electric current ratio α may be varied in order to generate action potentials/voltages within the first stimulation area R1, the second stimulation area R2 and the third stimulation area R3 of the nerve tissue, as shown in FIG. 3. Referring to FIGS. 8A-8C, an electric current ratio (1−α)I:αI is inputted into the nerve tissue through the conducting electrodes El.7, El.8. A higher $V_{ECAP'}$ corresponds to the denser area of the surviving nerve fibers distribution, and a lower $V_{ECAP'}$ corresponds to the less dense area of the surviving nerve fibers distribution. As shown in FIG. 8A, the conducting electrode El.7 has a higher $V_{ECAP'}$ and the conducting electrode El.8 has a lower $V_{ECAP'}$. According to another example of the present invention, the central position between the conducting electrode El.7 and the conducting electrode El.8 has a high $V_{ECAP'}$, as shown in FIG. 8B. According to an alternative example of the present invention, the conducting electrode El.8 has a higher $V_{ECAP'}$ and the conducting electrode El.7 has a lower $V_{ECAP'}$, as shown in FIG. 8C. As such, the normalized ECAP vs. distance reflects closely with the actual neural survival distribution (which is labeled Nf) in the top of each plot, as shown in FIGS. 8A-8C.

Compared to prior art, the electric current steering technique is incorporated with the normalized ECAP technique, a virtual electrode is formed between at least two input conducting electrodes by applying the electric current ratio to control electric current using an electric current steering device, in order to electrically stimulated nerve fibers within a plurality of stimulation areas of the nerve tissue. Accordingly, nerve fibers distribution can be quickly and precisely obtained based on the relationship between the normalized ECAP and the corresponding conducting electrodes.

Referring now to FIG. 9A, FIG. 9A shows a schematic diagram illustrating a structure of the ECAP without using the electric current steering technique. An electric current is inputted into the nerve tissue through the conducting electrode El.n. The conducting electrodes El.n−2, El.n−1, El.n+1, El.n+2, El.n+3 are used as the output conducting electrodes, as shown in FIG. 9A. V(t) represents a source action potential/voltage that is generated within the stimulation area R, and t represents time. In other words, V(t) generated in the centroid CEN of the stimulation area may be an ECAP $V_{ECAP'}$(t). Additionally, the electric potentials $Vs^{n-2}$, $Vs^{n-1}$, $Vs^{n+1}$, $Vs^{n+2}$, $Vs^{n+3}$ are received by the sensing conducting electrodes El.n−2, El.n−1, El.n+1, El.n+2, El.n+3, respectively.

According to equations (1) and (2), the distance between the adjacent conducting electrodes may be obtained prior to receiving $V_{ECAP'}$(t) within the stimulation area of the nerve tissue. As shown in FIG. 10A, the first voltage is inputted into the nerve tissue through an input conducting electrode. The plurality of output conducting electrodes receives the first electric potential in order to compute the distance between the adjacent conducting electrodes.

That is to say, when the distance D1 between the conducting electrode EL1 and the conducting electrode EL2 is obtained, an electric current IF is inputted through the conducting electrode EL1. The sensing (output) conducting electrodes EL2 and EL3 are used to receive the electric potentials V2' and V3'. Accordingly, k2 and the distance D2 between the conducting electrode EL1 and the conducting electrode EL3 can be computed by equation (3) and V2'·D1=k2·V1', V3'·D2=k2·V1' (wherein if the conducting electrodes are spherical, k2 is a constant). In addition, the attenuation factor may be computed based on the experimental result of electric potential vs. distance, as shown in FIGS. 6A-6E. If the conducting electrodes are spherical, $$DecayFactor(D) = \frac{k2}{D},$$

where k2 represents a constant. If the conducting electrodes are flat-shaped, the curve fitting method may be used to obtain the attenuation factor and angles of electric potentials and distance, as shown in FIGS. 6B-6E.

Figure 10B:
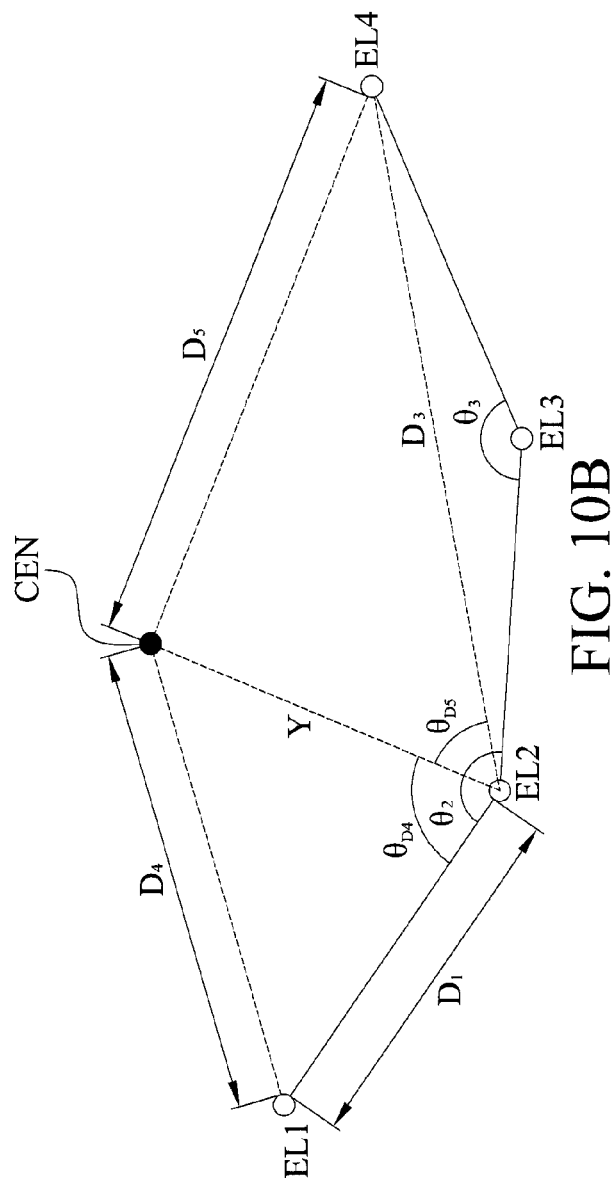
Figure 11:
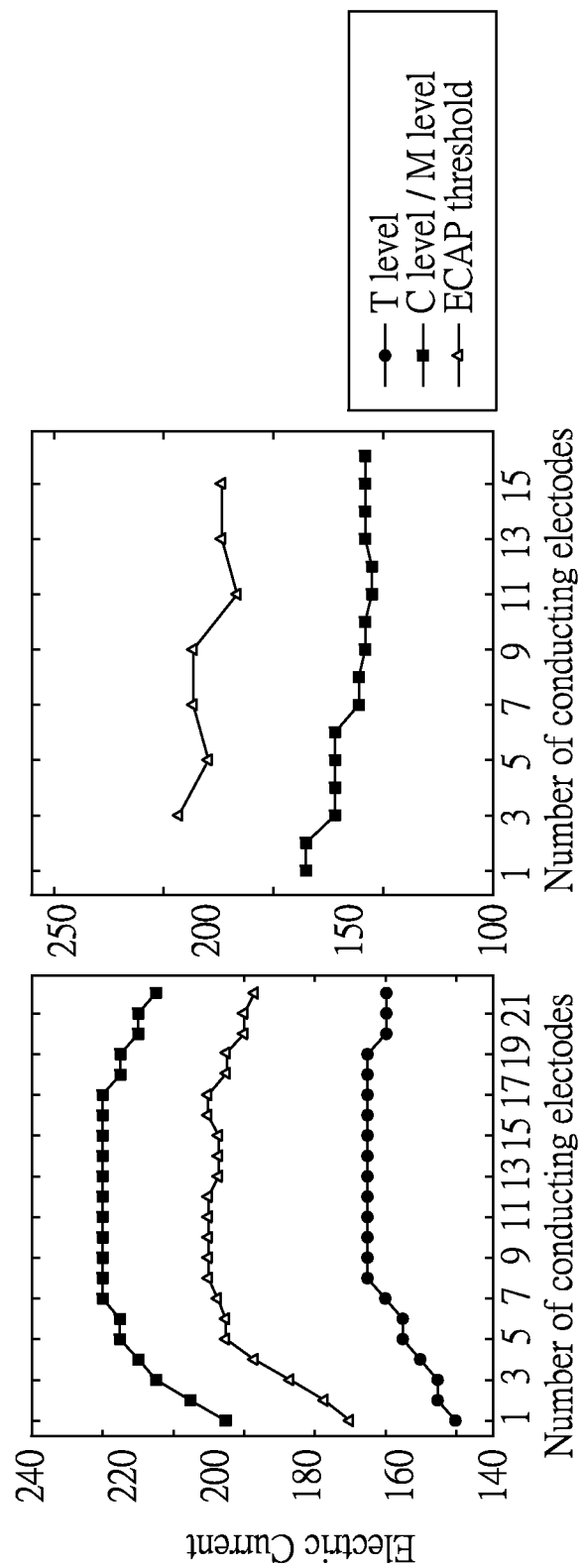
FIG. 11 shows plots of electric current vs. electrode illustrating the threshold (T) potential levels and the comfortable (C) potential level of electrical stimulation signal for a typical patient in the left plot, with a plot of ECAP threshold and the most (M) comfortable level shown on the right.

Moreover, as shown in FIG. 10B, the second voltage is inputted into the nerve tissue through an input conducting electrode. The plurality of output conducting electrodes receives the second electric potential in order to compute the distance between the adjacent conducting electrodes.

Specifically, an electric current is inputted into the nerve tissue through the conducting electrode EL2 in order to generate an ECAP $V_{ECAP'}$ in the centroid CEN of the nerve fiber. The other conducting electrodes EL1, EL3 and EL4 are used as the output conducting electrodes to receive electrical potentials V1, V3 and V4. The distance between the centroid CEN and the conducting electrode EL1 is labeled as D4, and the distance between the centroid CEN and the conducting electrode EL4 is labeled as D5. In one embodiment of the present invention, the distance Y may be computed by equation (7) based on D3, θ3, $\theta_{D5}$, $\theta_{D4}$ given. Once the distance Y is obtained, the distances will also be obtained.

$$D5 = \sqrt{Y^2 + D3^2 - 2Y \cdot D3 \cdot \cos\theta_{D5}}$$

$$D4 = \sqrt{Y^2 + D1^2 - 2Y \cdot D1 \cos\theta_{D4}} \quad (7)$$

Accordingly, the present invention provides a method for using a normalized evoked compound action potential (ECAP), comprising the steps of inputting a voltage signal into the nerve tissue through a plurality of conducting electrodes, and computing an average ECAP corresponding to a distance between each of the plurality of conducting electrodes and the nerve tissue based on the method for measuring a normalized ECAP (as shown in FIGS. 9-11); generating a curve of each of the plurality of conducting electrodes corresponding to the average ECAP; obtaining a threshold potential and a comfort potential of the voltage signal inputted into the nerve tissue, and obtaining a first correlation between the average ECAP and the threshold potential and a second correlation between the average ECAP and the comfort potential; generating the threshold potential level and the comfort potential level of each of the plurality of conducting electrodes based on the first correlation, the second correlation and the threshold potential and the comfort potential of the potential signal.

Referring to FIG. 11, FIG. 11 shows a plot of electric current vs. electrode illustrating the threshold (T) potential levels and the comfortable (C) potential level of electrical stimulation signal for a typical patient in the left plot. The ECAP threshold for each electrode is superimposed on the same plot. Notice the correlation between C and T level with ECAP threshold on the plot. The most (M) comfortable level of electrical stimulation signal for a typical patient is shown in the right plot. Again, notice the correlation between the M level with the ECAP threshold in this plot. As shown in FIG. 11, T level (threshold potential level) represents the minimum current a patient can hear, and C level (comfort potential level)/M level (most comfort potential level) represents the acceptable maximum current level a typical patient can hear without any problem. Generally, the ECAP threshold is between T level and C level/M level. In other words, the ECAP threshold is correlated with T level and C level/M level.

Consequently, the present invention provides a method for analyzing nerve fibers distribution using both the electric current steering technique and the normalized ECAP technique. Therefore, the threshold potential level and the most comfort potential level of an electrical stimulation signal for a patient can be quickly and precisely estimated without requiring the patient to respond. As such, the electric current stimulation factor can also be rapidly and precisely determined according to the method of the present invention.

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A method for analyzing nerve fibers distribution using a plurality of sensing and conducting electrodes on the surrounding of or inside a nerve tissue, comprising the steps of:
   (1) inputting a stimulation signal into the nerve tissue through at least two of the plurality of sensing and conducting electrodes, and applying a stimulation signal ratio to control the stimulation signal using an electric current steering technique to form at least one of a plurality of stimulation areas in the nerve tissue and to form at least one of a plurality of evoked compound action electric potentials (ECAPs) corresponding to at least one of the plurality of stimulation areas based on the stimulation signal ratio;
   (2) receiving at least two of the plurality of ECAPs using at least one of the plurality of sensing and conducting electrodes; and
   (3) computing a distribution angle corresponding to each of the plurality of sensing and conducting electrodes that are not used for inputting a voltage signal into the nerve tissue based on an electric potential attenuation factor, the voltage signal and the plurality of ECAPs, integrating and comparing the received at least two of the plurality of ECAPs to analyze the nerve fibers distribution in the nerve tissue based on the electric potential attenuation factor, a relative distribution of at least one of the plurality of sensing and conducting electrodes and a distance between a nerve fiber and at least one of the plurality of sensing and conducting electrodes within at least one of the plurality of stimulation areas.

2. The method of claim 1, wherein the nerve fibers distribution is obtained based on a distance between the nerve fiber and at least one of the plurality of sensing and conducting electrodes inputted by an electric current steering device and a distance between the nerve fiber and the other one of the plurality of sensing and conducting electrodes.

3. The method of claim 1, wherein a virtual electrode is formed between at least two of the plurality of sensing and conducting electrodes corresponding to the stimulation signal ratio for inputting an electric current.

4. The method of claim 1, wherein step (3) further comprises step (3-1) of: inputting the stimulation signal into the nerve tissue through one of the plurality of sensing and conducting electrodes and measuring at least one of the plurality of ECAPs through the other one of the plurality of sensing and conducting electrodes based on the electric potential attenuation factor, the relative distribution of at least one of the plurality of sensing and conducting electrodes and the distance between the nerve fiber and at least one of the plurality of sensing and conducting electrodes within at least one of the plurality of stimulation areas.

5. The method of claim 1, wherein the plurality of sensing and conducting electrodes are spherical sensing and conducting electrodes, and the electric potential attenuation factor is inversely proportional to the distance between the nerve fiber and at least one of the plurality of sensing and conducting electrodes within at least one of the plurality of stimulation areas.

6. The method of claim 1, wherein the plurality of sensing and conducting electrodes are flat-shaped sensing and conducting electrodes, and the electric potential attenuation factor is inversely proportional to the distance between the nerve fiber and at least one of the plurality of sensing and conducting electrodes within at least one of the plurality of stimulation areas.

7. The method of claim 1, wherein the plurality of stimulation areas cover different areas of the nerve tissue.

8. A method for analyzing nerve fibers distribution, comprising the steps of:
   (1) inputting a stimulation signal into a nerve tissue through at least two of a plurality of sensing and conducting electrodes, and applying a stimulation signal ratio to control the stimulation signal using an electric current steering technique to electrically stimulate a plurality of nerve fibers within a plurality of stimulations areas of the nerve tissue;
   (2) receiving a plurality of ECAPs using at least two of the plurality of sensing and conducting electrodes due to the plurality of nerve fibers electrically stimulated and computing a distance between one of the plurality of nerve fibers and at least two of the plurality of sensing and conducting electrodes; and
   (3) computing a distribution angle corresponding to each of the plurality of sensing and conducting electrodes that are not used for inputting a voltage signal into the nerve tissue based on an electric potential attenuation factor, the voltage signal and the plurality of ECAPs, and integrating and comparing the received plurality of ECAPs to analyze the nerve fibers distribution of the nerve tissue.

9. The method of claim 8, wherein in step (2) the distance between the one of the plurality of nerve fibers and at least two of the plurality of sensing and conducting electrodes received is computed using a triangulation technique and a ratio relationship of the plurality of ECAPs to the distance.

10. The method of claim 8, wherein the nerve fibers distribution is obtained based on a distance between the one of the plurality of nerve fibers and at least two of the plurality of sensing and conducting electrodes inputted by an electric current steering device and a distance between the one of the plurality of nerve fibers and the other one of the plurality of sensing and conducting electrodes.

11. The method of claim 8, wherein a virtual electrode is formed between at least two of the plurality of sensing and conducting electrodes corresponding to the stimulation signal ratio for inputting an electric current.

12. A method for measuring a normalized evoked compound action potential (ECAP), comprising the steps of:
  (1) inputting a voltage signal into a nerve tissue through at least one of a plurality of sensing and conducting electrodes, and computing a distribution angle corresponding to each of the plurality of sensing and conducting electrodes that are not used for inputting the voltage signal into the nerve tissue based on an electric potential attenuation factor, the voltage signal and a plurality of ECAPs;
  (2) computing a distance between a nerve fiber and each of the plurality of sensing and conducting electrodes based on the distribution angle corresponding to each of the plurality of sensing and conducting electrodes;
  (3) inputting a stimulation signal into the nerve tissue through at least one of the plurality of sensing and conducting electrodes to generate the plurality of ECAPs, receiving the plurality of ECAPs using the other one of the plurality of sensing and conducting electrodes that are not used for inputting the stimulation signal into the nerve tissue, and receiving the plurality of ECAPs corresponding to the other one of the plurality of sensing and conducting electrodes based on the distance between the nerve fiber and each of the plurality of sensing and conducting electrodes including the electric potential attenuation factor; and
  (4) computing the received plurality of ECAPs to obtain an average ECAP of the nerve fiber.

13. The method of claim 12, wherein the distance is between a centroid of the nerve fiber and each of the plurality of sensing and conducting electrodes, and the average ECAP of the nerve fiber is computed based on the centroid of the nerve fiber.

14. The method of claim 12, wherein step (1) further comprises inputting the voltage signal into the nerve tissue through at least one of the plurality of sensing and conducting electrodes and computing the distribution angle corresponding to each of the plurality of sensing and conducting electrodes that are not used for inputting the voltage signal into the nerve tissue; measuring resistances between any two adjacent ones of the sensing and conducting electrodes; and computing a nerve fibers distribution corresponding to the plurality of sensing and conducting electrodes based on the voltage signal, the plurality of ECAPs and the resistances.

15. The method of claim 12, wherein step (2) further comprises computing the distance between the nerve fiber and each of the plurality of sensing and conducting electrodes using a triangulation technique based on the distribution angle corresponding to each of the plurality of sensing and conducting electrodes.

16. The method of claim 12, wherein the plurality of sensing and conducting electrodes are spherical sensing and conducting electrodes, and the electric potential attenuation factor is inversely proportional to the distance between the nerve fiber and each of the plurality of sensing and conducting electrodes.

17. The method of claim 12, wherein the plurality of sensing and conducting electrodes are flat-shaped sensing and conducting electrodes, and the electric potential attenuation factor is inversely proportional to the distance between the nerve fiber and each of the plurality of sensing and conducting electrodes.

18. A method for using a normalized evoked compound action potential (ECAP), comprising the steps of:
  (1) inputting a voltage signal into the nerve tissue through a plurality of sensing and conducting electrodes, and computing an average ECAP corresponding to a distance between each of the plurality of sensing and conducting electrodes and the nerve tissue based on a method for measuring a normalized ECAP, wherein the method for measuring the normalized ECAP comprises computing a distribution angle corresponding to each of the plurality of sensing and conducting electrodes that are not used for inputting the voltage signal into the nerve tissue based on an electric potential attenuation factor, the voltage signal and a plurality of ECAPs;
  (2) generating a curve of each of the plurality of sensing and conducting electrodes corresponding to the average ECAP;
  (3) obtaining a threshold potential and a comfortable potential level of the voltage signal inputted into the nerve tissue, and obtaining a first correlation between the average ECAP and the threshold potential and a second correlation between the average ECAP and the comfortable potential level, wherein the comfortable potential level represents an acceptable maximum current level; and
  (4) generating a threshold potential level and a comfortable potential level of each of the plurality of sensing and conducting electrodes based on the first correlation, the second correlation and the threshold potential and the comfortable potential level of the voltage signal.

19. The method of claim 18, wherein the method of measuring the normalized ECAP of step (1) comprises the steps of:
  (1-1) inputting the voltage signal into the nerve tissue through at least one of the plurality of sensing and conducting electrodes;
  (1-2) computing the distance between the nerve fiber and each of the plurality of sensing and conducting electrodes based on the distribution angle corresponding to each of the plurality of sensing and conducting electrodes;
  (1-3) inputting a stimulation signal into the nerve tissue through at least one of the plurality of sensing and conducting electrodes to generate the plurality of ECAPs, receiving the plurality of ECAPs using the other one of the plurality of sensing and conducting electrodes that are not used for inputting the stimulation signal into the nerve tissue and computing the plurality of ECAPs corresponding to the other one of the plurality of sensing and conducting electrodes, based on the plurality of ECAPs, the distance between the nerve fiber and each of the plurality of sensing and conducting electrodes, and the electric potential attenuation factor; and
  (1-4) computing the received plurality of ECAPs to obtain an average ECAP of the nerve fiber.

* * * * *